United States Patent [19]
Kroll et al.

[11] Patent Number: 5,899,923
[45] Date of Patent: May 4, 1999

[54] AUTOMATIC CAPACITOR MAINTENANCE SYSTEM FOR AN IMPLANTABLE CARDIOVERTER DEFIBRILLATOR

[75] Inventors: Mark W. Kroll, Minnetonka; Ann M. Donohoo, Shorview, both of Minn.

[73] Assignee: Angeion Corporation, Plymouth, Minn.

[21] Appl. No.: 08/620,390

[22] Filed: Mar. 22, 1996

[51] Int. Cl.$^6$ .................................................. A61N 1/39
[52] U.S. Cl. .................................................. 607/5
[58] Field of Search .......................... 607/5, 27, 29, 607/39

[56] References Cited

U.S. PATENT DOCUMENTS

| | | |
|---|---|---|
| 4,134,408 | 1/1979 | Brownlee et al. . |
| 4,324,251 | 4/1982 | Mann . |
| 4,345,603 | 8/1982 | Schulman . |
| 5,137,020 | 8/1992 | Wayne et al. . |
| 5,163,428 | 11/1992 | Pless ............................................ 607/5 |
| 5,312,444 | 5/1994 | Bocek et al. ................................ 607/5 |
| 5,350,405 | 9/1994 | Silvian ...................................... 607/27 |
| 5,369,364 | 11/1994 | Renirie et al. . |
| 5,370,668 | 12/1994 | Shelton et al. . |
| 5,391,193 | 2/1995 | Thompson . |
| 5,405,363 | 4/1995 | Kroll et al. . |
| 5,407,444 | 4/1995 | Kroll ........................................... 607/5 |
| 5,411,537 | 5/1995 | Munshi et al. . |
| 5,439,482 | 8/1995 | Adams et al. . |
| 5,458,997 | 10/1995 | Crespi et al. . |
| 5,554,174 | 9/1996 | Causey, III . |

OTHER PUBLICATIONS

U.S. application No. 08/549,284, Oct. 27, 1995, Kroll et al.

*Primary Examiner*—William E. Kamm
*Assistant Examiner*—George R. Evanisko
*Attorney, Agent, or Firm*—Brad Pedersen

[57] ABSTRACT

An automatic capacitor maintenance system for an implantable cardioverter defibrillator (ICD) reforms the capacitor system of the ICD based on measurements relating a current leakage and a charge time of the capacitor system as determined at a stable low voltage state. Preferably, differential changes in current leakage across the capacitor system are monitored and the capacitor system is reformed based on a pre-set estimated charge time. The automatic capacitor maintenance system produces significant savings in the amount of battery energy consumed to reform the capacitor system of an ICD, while maintaining the capacitor system at an optimum charging efficiency so as to insure high reliability of both the capacitor system and the ICD.

19 Claims, 7 Drawing Sheets

AUTOMATIC CAPACITOR MAINTENANCE SYSTEM FOR AN IMPLANTABLE CARDIOVERTER DEFIBRILLATOR

TECHNICAL FIELD

The present invention relates generally to an implantable cardioverter defibrillator (ICD) devices. More particularly, the present invention relates to an automatic capacitor maintenance and reforming apparatus and method specifically tailored to reform the high voltage capacitor systems.

BACKGROUND OF THE INVENTION

The use of implantable cardioverter defibrillator (ICD) devices that deliver an electrical counter shock from a charge stored in a high voltage capacitor system so as to treat cardiac arrhythmia is well known. The capacitor systems in all present ICD devices which have been approved for use in humans utilize capacitors that are of the aluminum electrolytic type. While aluminum electrolytic capacitors provide high energy density per unit volume, they tend to degrade electrochemically over time and need to be reformed frequently to maintain optimum capacitor-discharge. This need for frequent reforming results in the need for larger power supplies for the ICD, which in turn increase the size of the ICD. Accordingly, it would be desirable to provide a capacitor maintenance system for aluminum electrolytic capacitors which decreases the power demands of frequent reforming.

ICDs use capacitor-discharge systems that generate high energy cardioversion/defibrillation countershocks by using a low voltage battery to charge a capacitor system over a relatively long time period (i.e. seconds) with the required energy for the defibrillation countershock. Once charged, the capacitor system is then discharged for relatively short, truncated time period (i.e. milliseconds) at a relatively high discharge voltage to create the defibrillation countershock that is delivered through implantable electrode leads which discharge current into the heart muscle of a human patient.

Presently, all capacitor-discharge ICDs are designed such that the capacitor system can store a maximum electrical charge energy of at least about 25 joules. This requirement imposes a need to maintain the capacitor system at optimum performance levels. Accordingly, aluminum electrolytic capacitors must be reformed and maintained at peak capacity. A typical reforming regimen is to charge the capacitor up to its full rated voltage and then allow the accumulated voltage to trickle off. This process electrochemically reforms the oxide in the capacitor anode so as to enable a more efficient capacitive discharge. When the capacitor system has gone a long time without reforming, the charge time to attain a maximum voltage on a charge can increase significantly. Typically, for example, the charge time could increase from five seconds to ten seconds in a period of one or two years. A worst case scenario is when the charge time could be as long as thirty seconds or more when the battery system used to charge the capacitor system is near its end of life. This increase in the charge time could be detrimental to a human patient who needs a full charge defibrillation shock immediately.

Early ICD devices contained robust battery systems with large energy reserves. Therefore, these devices had excessive battery energy which was not affected by the need to reform the capacitor system. Further, these devices had a short service life which made reforming a less critical energy concern because the devices were discarded long before the battery energy was exhausted. In sharp contrast, current ICD devices use compact batteries with a limited energy budget that are designed to last for a relatively long time. Both space and volume requirements favor small batteries in ICDs. The state of the art in battery technology, however, is such that compact batteries do not hold a large energy reserve. Capacitor reforming using these small batteries can consume a significant portion of the scant energy reserve. Presently, the automatic reforming features of all ICD's are based on a set time period. This automatic reforming strictly uses time intervals between scheduled maintenance cycles to determine when to reform the capacitor system.

SUMMARY OF THE INVENTION

The present invention is a capacitor maintenance system for an implantable cardioverter defibrillator (ICD) which enables conservation of expensive battery energy by reforming the capacitor system only in response to an automatic monitoring of the capacitor system. An automatic monitoring mechanism in the ICD periodically determines the need to reform the capacitor system such that the capacitor is maintained at peak performance to thereby reliably deliver power to the ICD upon demand. Specifically, the automatic monitoring system periodically measures current leakage in the capacitor system in order to make a more intelligent determination as to when the capacitor system needs reforming.

Specific advances, features and advantages of the present invention will become apparent upon examination of the following description and drawings dealing with several specific embodiments thereof.

DESCRIPTION OF THE PREFERRED EMBODIMENT

Figure 1:
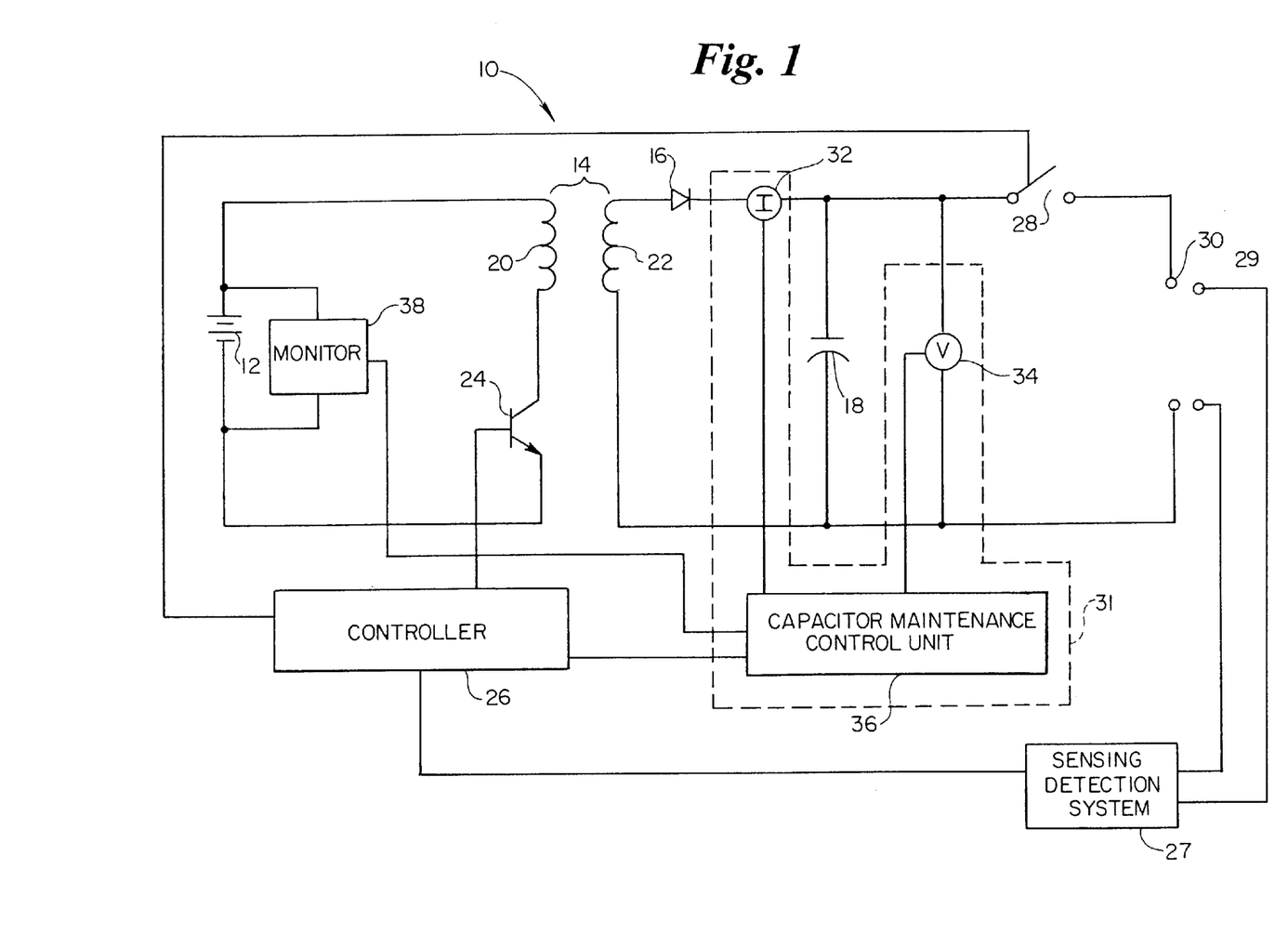
FIG. 1 shows a schematic of the basic components of an ICD device with the elements of the present invention included.

Referring to FIG. 1 of the drawings, an ICD circuit 10 comprising electronic components and their relative connections are shown. The ICD circuit 10 generally includes: a battery system 12, a transformer 14, a diode 16 and a capacitor system 18 to transfer current from the battery 12 through a low voltage primary side 20 of transformer 14 to a high voltage secondary side 22 of transformer 14 in order to develop a charge on capacitor 18. Transistor 24 is used to switch the current from the battery 12 into the transformer 14, under control of microprocessor 26. An output switching network (shown for convenience as a single switch at 28) is operated under control of microprocessor 26, and discharges the electrical charge stored in the capacitor system 18 through a plurality of implantable electrode terminals 30 in response to a detection of a cardiac arrhythmia by sensing system 27 based on cardiac activity obtained from sensing electrodes 29. For a more detailed description of the design and operation of an ICD, reference is made to U.S. Pat. No. 5,405,363 which is incorporated herein by reference.

In the present invention, an automatic capacitor maintenance discharge system 31 includes a current meter 32 that is wired in series with diode 16 and capacitor 18 and/or a voltmeter 34 that is connected across terminals 30. Capacitor maintenance discharge system 31 comprises components shown in block diagrams for illustration purposes. The components include either or both of current meter 32 and voltage meter 34 and a control unit 36 which monitors and registers voltage and current measurements from the current meter 32 and/or voltage meter 34, such as by use of an analog-to-digital converter. Control unit 36 can include a microprocessor to control the software routine and perform algorithmic calculations, and circuitry to trigger and terminate a reform cycle. It will be understood that control unit 36 can be implemented as separate, independent control systems to perform each function, or that portion of the function of control unit 36 can be incorporated into the operation of a single microprocessor within the ICD which preferably also performs the functions of controller 26.

As transistor 24 is closed by controller 26 during a charging cycle, battery system 12 is directly connected to the primary coil 20 of transformer 14. When transformer 24 is opened, a high voltage is produced in the transformer secondary. This voltage is directed through diode 16 to charge capacitor 18. Current meter 32 records the current in the circuit and voltmeter 34 registers the system voltage when the charging cycle is completed.

Figure 2:
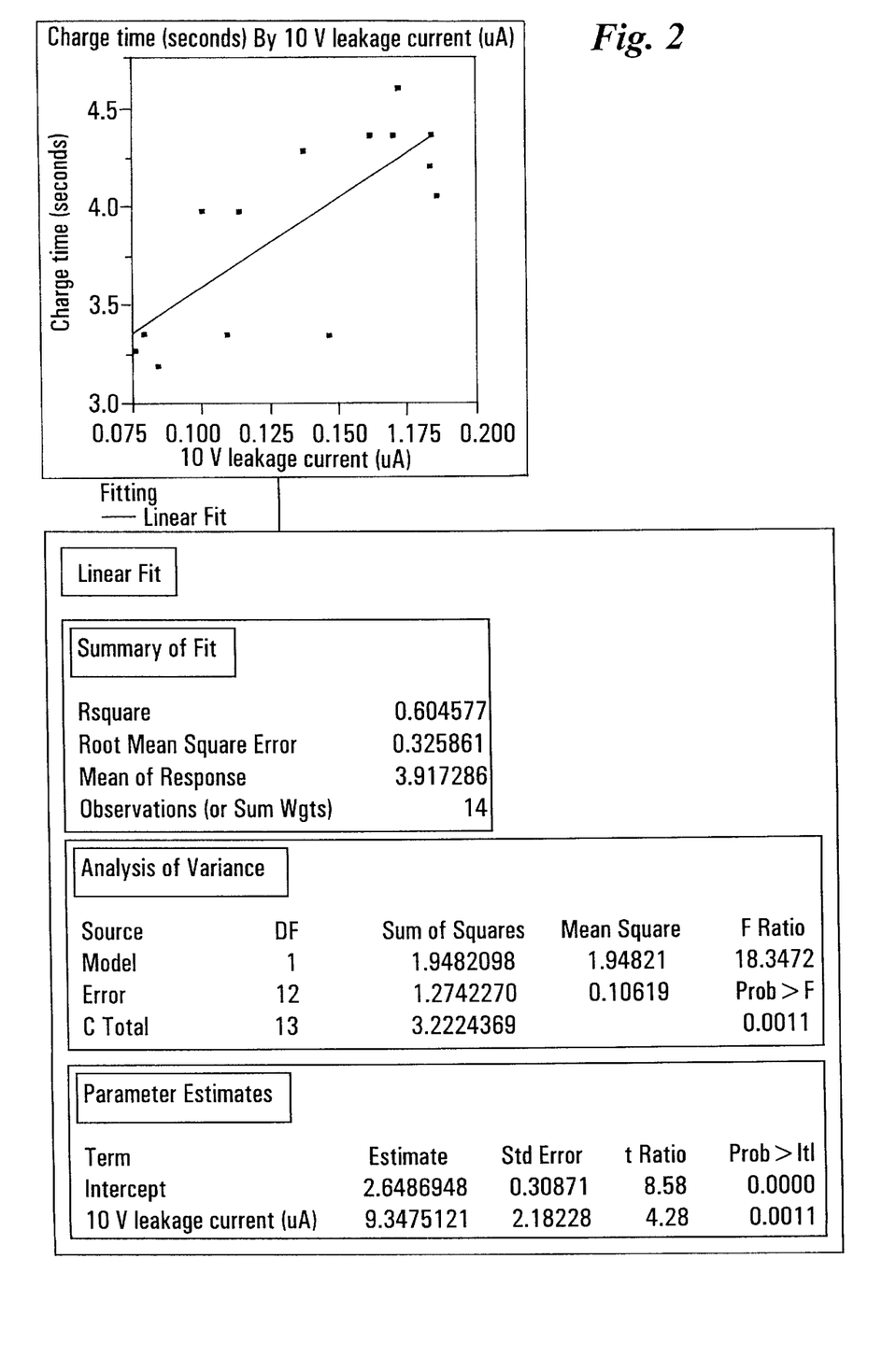
FIG. 2 is a graphical representation of a charge time in seconds versus leakage current based on a 10 volt test

Tests conducted by the inventors have shown that leakage current of a photoflash electrolytic capacitor at 10 volts is a reasonably accurate indication of a need for reforming. Moreover, leakage currents at 30 volts are found to yield a very accurate indication of the need for reforming. Referring to FIG. 2, a graphical representation of charge time in seconds versus leakage current based on a 10 volt test is shown. Data comprising 14 observations relating to charge time in seconds versus the 10 V leakage current (uA) are plotted as shown. The data is linearly fitted using a least squares method. The capacitor charge time can be determined to within an $r^2=0.60$. Utilizing the parameter estimates, charge time is calculated as the sum of the intercept and the corresponding value of the 10 volt leakage current, which is 9.35 seconds for each micro ampere of 10 volt leakage. Thus, if the calculated charge time is found to lie beyond a critical value, then a reforming cycle would be initiated by control unit 40. On the other hand, if the calculation yields a value below a set critical value, there will be no need for reforming and battery energy will not be unnecessarily squandered. The energy required to charge a capacitor to a 10 volt state is about 0.01 joules. This is significantly less when compared to the energy required to fully reform a capacitor system 18, which is at least about 25 Joules. Accordingly, the present invention enables to determine the need for reforming a capacitor system without committing large amounts of energy.

Figure 3:
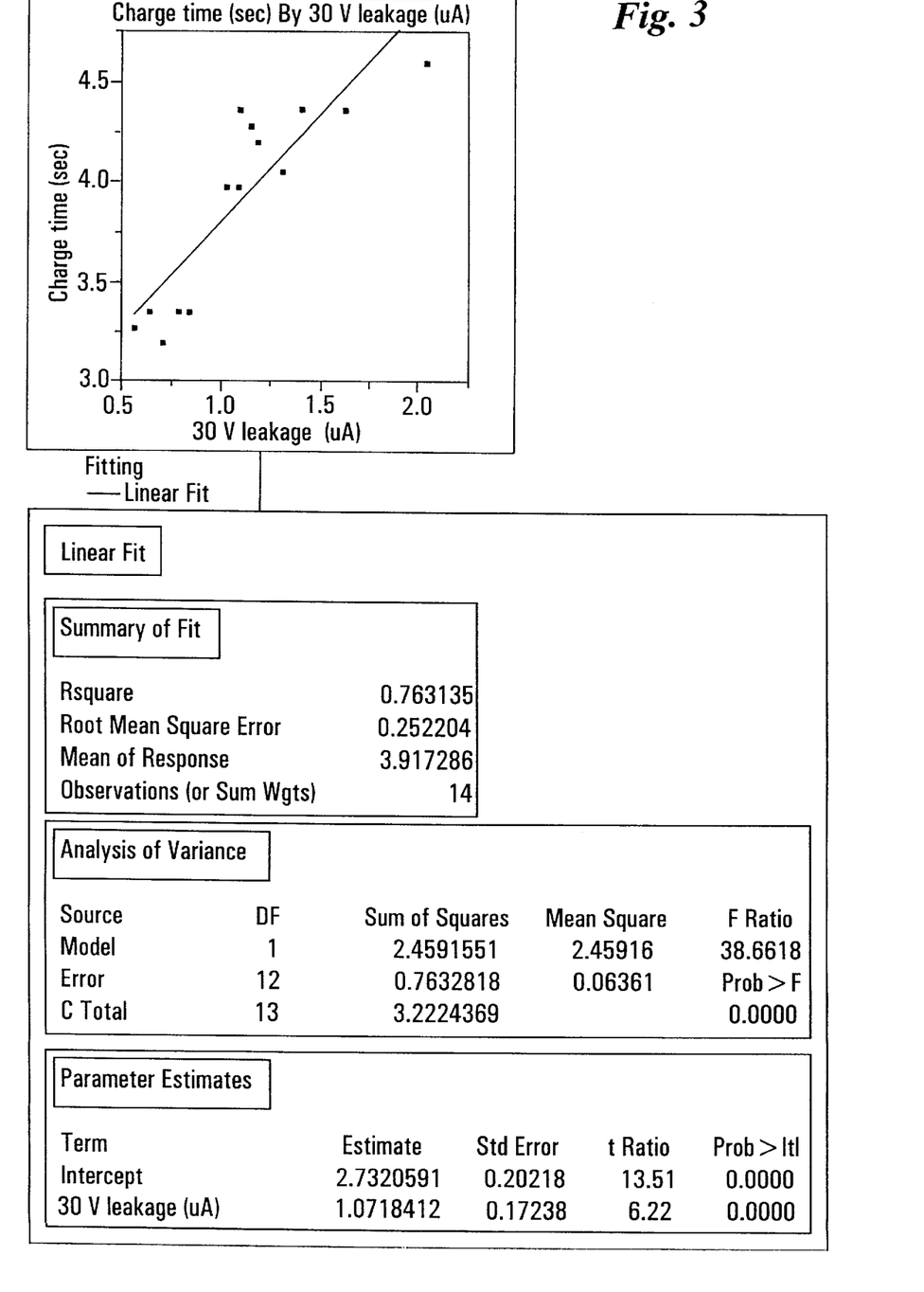
FIG. 3 is a graphical representation of charge time in seconds versus leakage current based on a 30 volt test.

Similarly, FIG. 3 is a graphical representation of charge time in seconds versus leakage current based on a 30 volt test. Data comprising 14 observations is plotted and the data is fitted to within $r^2=0.76$. Thus using the parameter estimates, charge time is the sum of the intercept and the corresponding value of the 30 volt leakage, which is 1.07 seconds for each micro ampere. In other words, the intercept value of 2.7 seconds is added to the microampere of leakage at 30 volt. This value could be a trigger point for reforming the capacitor system. For example, if the sum suggests a value greater than a predetermined value, a capacitor reforming cycle can be initiated by the control unit 36 and carried out by controller 26.

Figure 4:
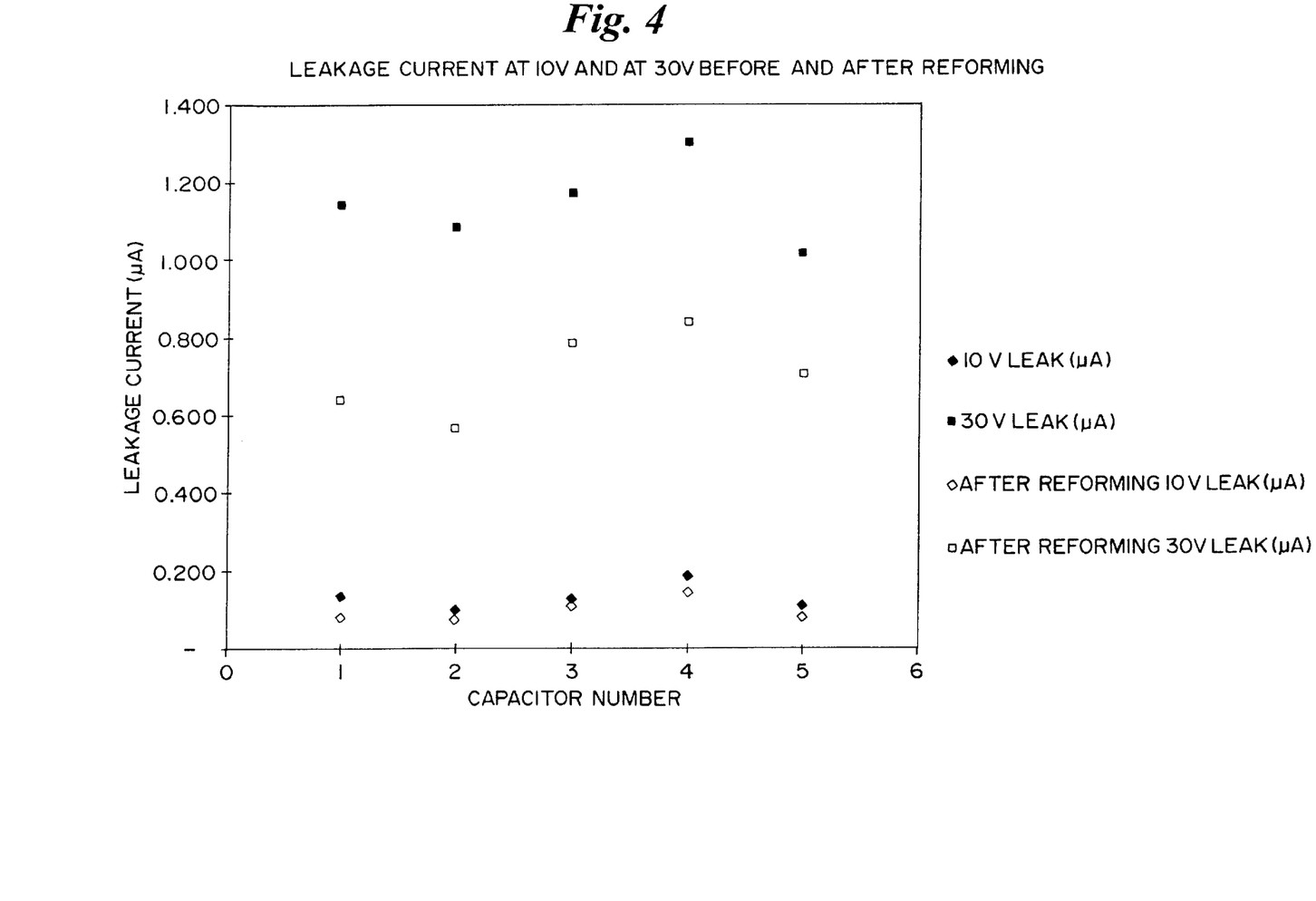
FIG. 4 is a graphical representation of leakage current at 10 Volt and at 30 volts before and after reforming for a specified capacitor.

Further, FIG. 4 shows leakage current at 10 volt and 30 volt, for different capacitor system, before and after reforming. The plot indicates that the current leakage is positively related to the voltage. Thus, lower voltages exhibit relatively low leakage currents. The point of FIG. 4 is that the leakage current test is also an exposed facto correlate of the need to reform, i.e., they both go down together.

Figure 5:
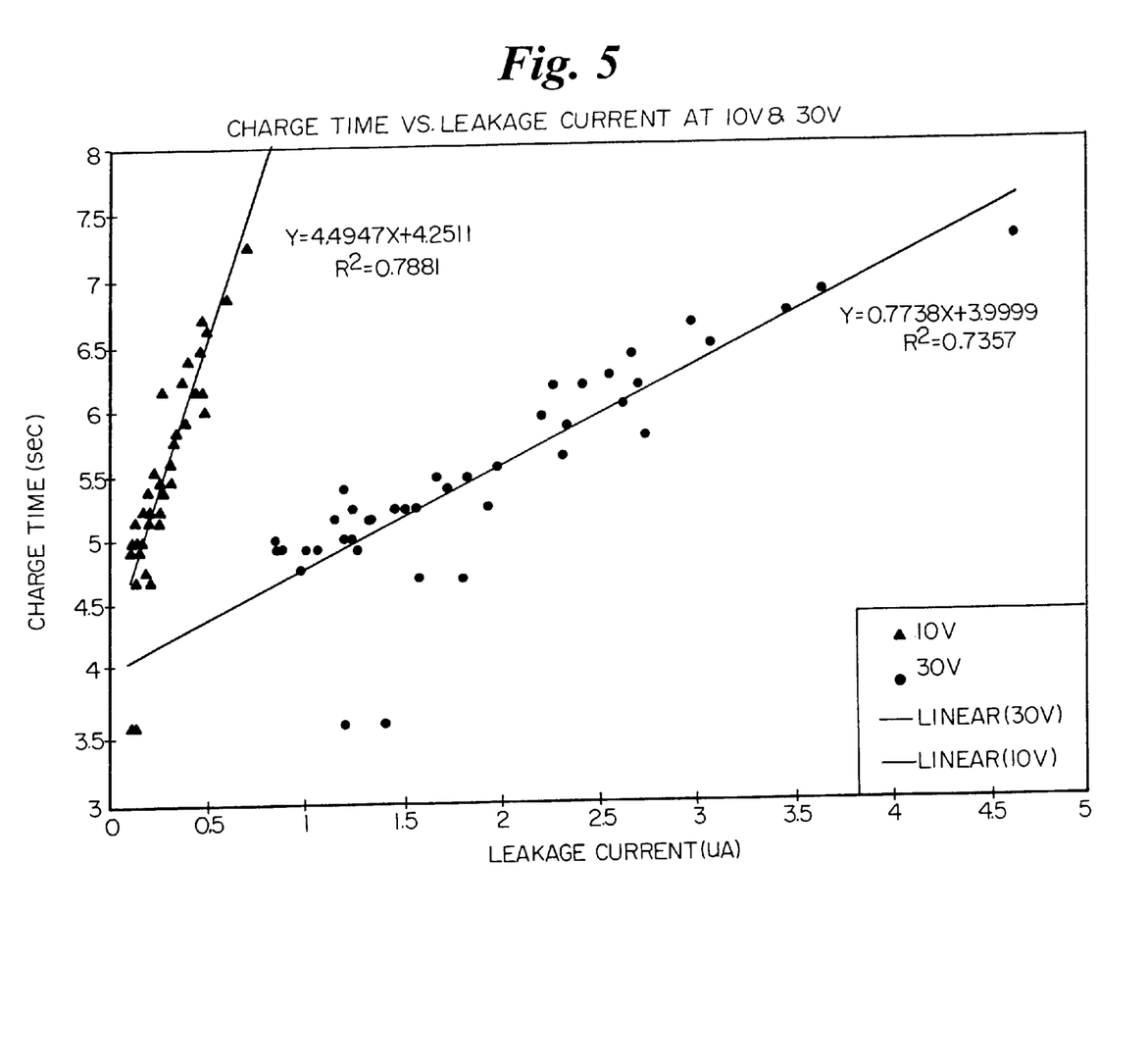
FIG. 5 is a graphical representation of the charge time in seconds versus leakage current based on 10 volt and 30 volt tests.

FIG. 5 is a graphical representation of charge time versus leakage current for 10 and 30 volt tester.

Figure 6:
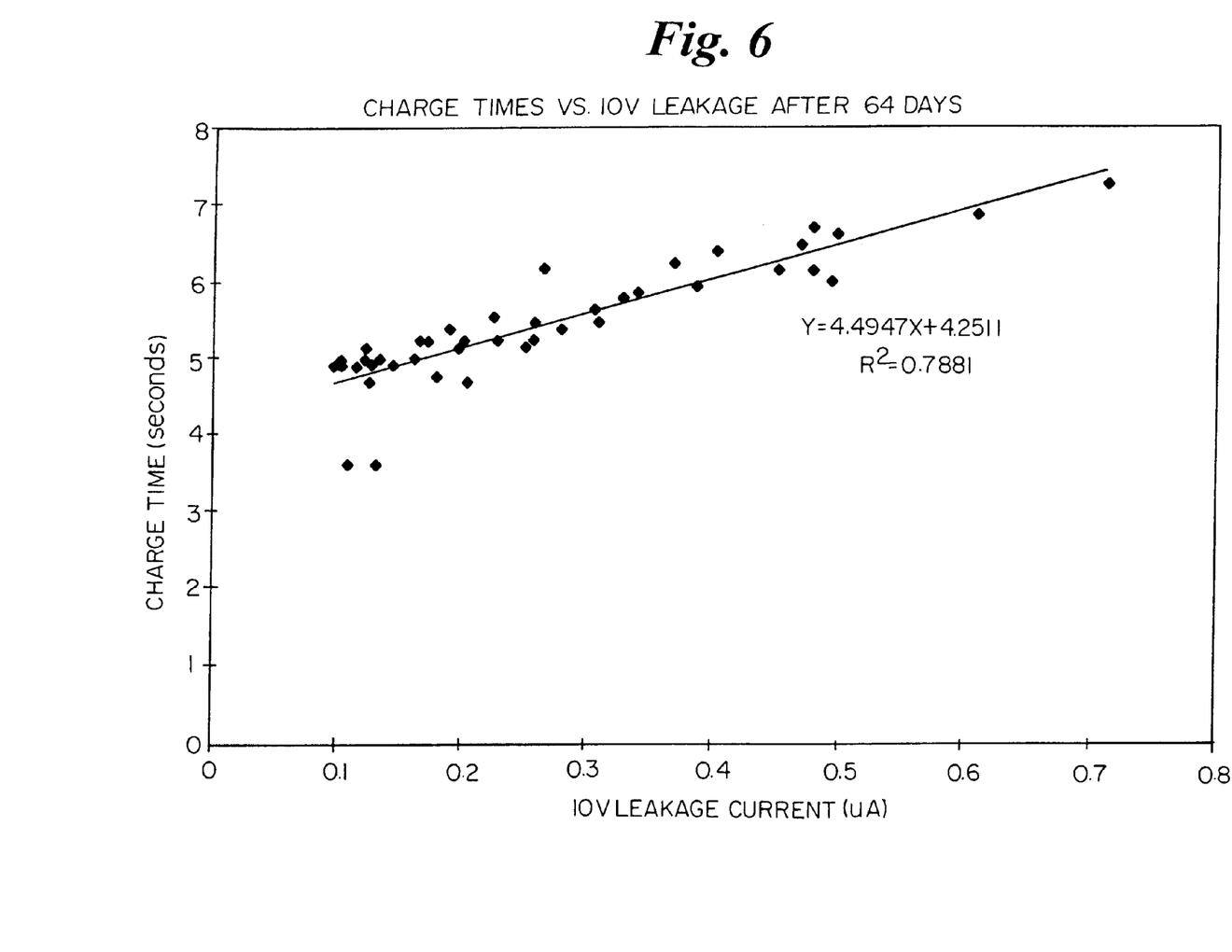
FIG. 6 is a graphical representation of charge time in seconds versus leakage current based on a 10 volt test, 64 days after reforming.

FIG. 6 shows a charge time versus 10 volt leakage after 64 days. The graph confirms the earlier experimental findings and provides a strong analytical basis for the reforming factors and parameters advanced by the present invention. Significantly, it shows a higher level of correlation of $r^2=0.79$. More significantly, previous values disclosed in FIGS. 2 through 4 relate to observations made ranging from a few days to about a week. The data in FIG. 6 spans a period of over two months and provides a high confidence level in using charge time and current leakage as a basis for scheduling a reforming cycle for the capacitor system. Accordingly, the observations, method and device of the present invention conclusively teach that the leakage current can be used as an indication to determine reforming cycles of a capacitor. Particularly, the present invention enables detection of small leakage currents using a low voltage in capacitor system 18.

Figure 7:
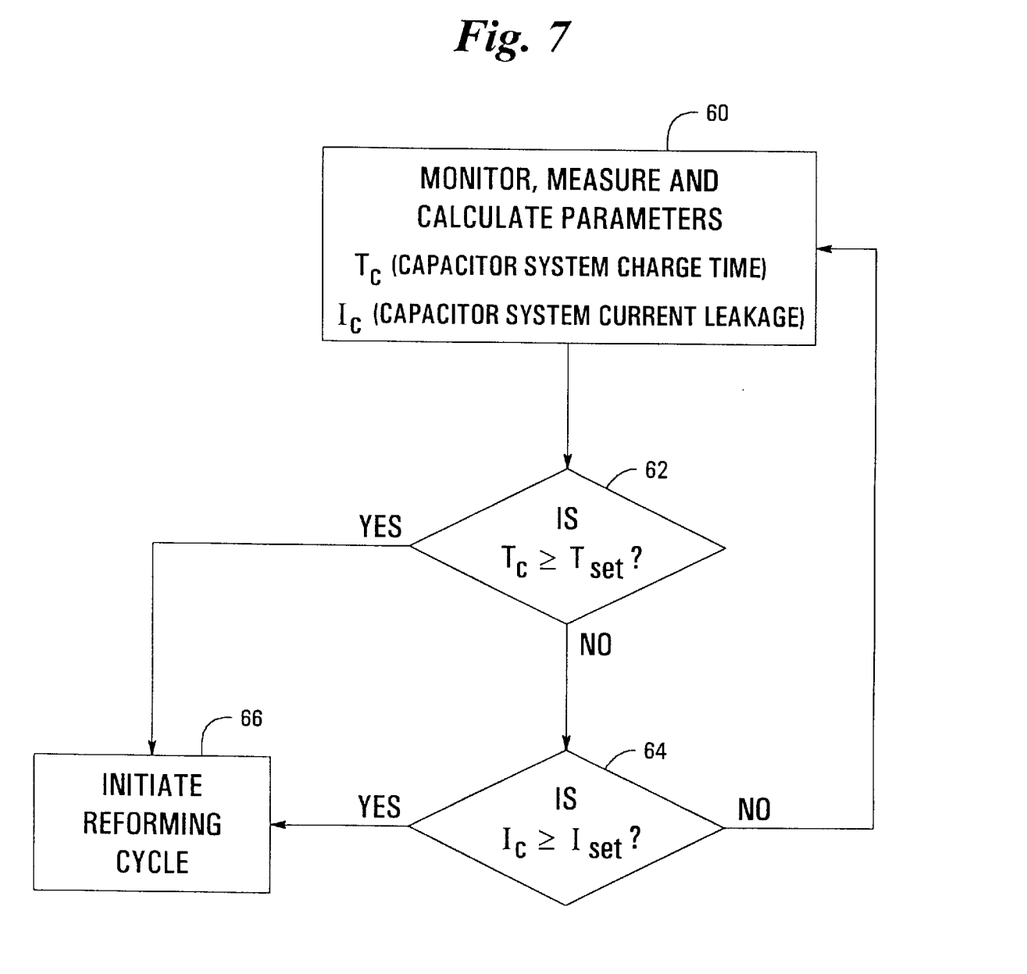
FIG. 7 is a flow chart showing logic steps and routines for monitoring and reforming cycles.

The operations of the present invention include, generally, reading the current at a low stable voltage. Any increase in the current over a stored threshold is then noted and a reforming cycle is initiated. FIG. 7 is a flow chart showing an embellished and alternative embodiment. Initially, logic step 60 measures electrical parameter which include $T_c$ (capacitor system charge time) and $I_c$ (capacitor system current leakage). These inputs are collected by having controller 26 charge the capacitor system 18 to a low voltage. The control unit 36 utilizes the current meter 32, for example, to measure $I_c$ over $H_c$ and uses the voltage meter 34, for example, to measure the system voltage to determine the charging time to a given voltage, and compares these values to preset values of charge time and current ($T_{set}$ and $I_{set}$) and proceeds to logic step 62 in the software. At this point, the software investigates if $T_c$ (Capacitor charge time) is greater or equal to $T_{set}$ (preset charge time). If $T_c$ is indeed equal to or greater than $T_{set}$ it means the capacitor system 18 needs to be reformed before it reaches a critical point at which the reforming will take a significantly long charge time as to endanger the patient's safety. Thus, the capacitor system will be reformed under logic step 66. If, however, $T_c$ is not greater or equal to $T_{set}$, the routine proceeds to logic step 64. Here, the software investigates whether, $I_c$ (Capacitor system leakage current) is greater than or equal to $I_{set}$. If the capacitor leakage current greater than or equal to the preset current value, the system calls for a capacitor reform cycle under logic step 66. If, on the other hand, the capacitor system current is found to be less than $I_{set}$ the routine proceed to logic step 60.

One of the distinguishing features of the automatic capacitor maintenance discharge system 31 of the present invention is the current meter 32 which is coupled in series to diode 16 and capacitor system 18. The difference between the two voltage readings over time can also yield a measure of the current leakage. It should be noted that the average current leakage is about 1.2 µA with a 30 volt test before reforming. After capacitor system 18 is reformed the current reading drops to an average value of 0.7 µA (shown as open square boxes). Similarly, for the 10 volt system, the leakage current shows a predictable variation. The present invention utilizes the principals of this phenomenon to implement a capacitor reforming device and method by monitoring and comparatively measuring leakage current at a stable low voltage such that the prior practice of committing vast amounts of energy to reform a capacitor is eliminated except when needed. As indicated hereinabove, the energy used in recharging capacitor system 18 to a low voltage is rather insignificant when compared to the energy required to reform a capacitor system in accordance with prior practice. Thus, the present invention provides a device and method in which minute changes in the electrical characteristics of the capacitor system are monitored and corrected through a timely reforming regimen such that significant energy savings and ICD reliability are achieved.

An embodiment of the present invention may be structured to monitor minute variations in current and replenish the capacitor system 18 up to that current level by charging capacitor system 18 at a low voltage of less than 100 volts whenever a predetermined value is not met and continuing charging until that predetermined value is met on a continuous level. For example, control unit 36 may be structured to run a continuous routine and in cooperation with the controller 26 to continuously determine an estimated charge time (from a given current leakage reading at a constant low voltage). Thus, the capacitor system 18 may be charged if the data exceeds a certain charge time. Charge time is a critical parameter both for the reliability of the ICD and the state of the capacitor system 18 and battery system 12. The ICD unit has to be in an ever-ready state to deliver a shock when needed. If charge time is too long, the safety of the patient may be compromised. The present invention provides means and methods to overcome this technical difficulty in the operation of ICD capacitors particularly over long periods of time.

Yet another alternate embodiment of the present invention may incorporate a monitor 38 to check the state-of-charge of the battery 12. The system may include an indicator to read the state of charge and compare it to a state of charge of an ideal battery or new battery. Knowing the state-of-charge of the battery, the system may charge a relatively inefficient or leaky capacitor more often when the battery is new. On the other hand, if the battery is old (for example when the ICD is nearing its life cycle), then the battery performance has degraded substantially and the need for the capacitor system to be maintained at peak capacity becomes apparent so as to avoid the worst case charge time with the capacitor systems.

Having thus described the preferred embodiment of the present invention, those skilled in the art will readily appreciate the many other embodiments which can be employed within the scope of the claims provided below.

What is claimed is:

1. An automatic capacitor maintenance device for an implantable cardioverter defibrillator (ICD) system, the ICD system being a self contained implantable device including a capacitor system, a battery system, and a sensing system, all of which are connected to and controlled by a control system which charges the capacitor system from the battery system and discharges the capacitor system through a plurality of implantable electrodes to treat a cardiac arrhythmia as sensed by the sensing system, the automatic capacitor maintenance device comprising:
   means for measuring at least one electrical parameter of said capacitor system; and
   means for initiating a capacitor reforming cycle of said capacitor system in response to said means for measuring.

2. The device of claim 1, wherein said means for measuring electrical parameters includes a voltmeter connected across said plurality of electrodes.

3. The device of claim 1, wherein said means for measuring electrical parameters includes a current meter connected in series to a diode and said capacitor system.

4. The device of claim 1, wherein said means for initiating includes means for monitoring and registering a leakage current of said capacitor system and comparing said leakage current to a predetermined value to trigger said reforming cycle for said capacitor system.

5. The device of claim 1, wherein said means for initiating includes means for calculating an estimated charge time of said capacitor system to a high voltage value based on said at least one electrical parameter measured by said means for measuring at a low voltage value applied to said capacitor system to thereby determine the need for reforming said capacitor system.

6. The device of claim 1, wherein said capacitor reforming cycle is comprised of charging said capacitor system from said battery system at a voltage of less than 100 volts until said at least one electrical parameter measured by said means for measuring returns to a predetermined nominal value.

7. The device of claim 1, wherein said means for initiating includes a microprocessor which statistically determines an estimated charge time based on said at least one electrical parameter measured by said means for measuring and comparing said estimated charge time to a predetermined maximum charge time to thereby initiate said capacitor reforming cycle.

8. The device of claim 1, further comprising monitor means connected to said battery system and said means for initiating for monitoring an electrical parameter of said battery system, wherein said means for initiating alters said capacitor reforming cycle in response to said electrical parameter of said battery system.

9. The device of claim 1, wherein said means for initiating includes a programmable means to generate root mean square values for a leakage current of said capacitor system measured over a period of time by said means for measuring in response to a low voltage charge applied to said capacitor and compare said root mean square values to a predetermined value to thereby determine whether to initiate said capacitor reforming cycle.

10. An automatic capacitor maintenance and reforming device for use in implantable cardioverter defibrillator (ICD) device wherein said ICD device is a self contained implantable device including a battery system, a capacitor system, and a sensing system all of which are connected to and controlled by a control system which, in response to a cardiac dysrhythmia as sensed by the sensing system, charges the capacitor system from the battery system and then discharges the capacitor system to be delivered as a high voltage pulse to a plurality of implantable electrodes, the device comprising:
   means for monitoring and correlating a charge time of said capacitor system with a leakage current measured for said capacitor system; and
   means for initiating a reforming cycle of said capacitor system based on results from said means for monitoring and correlating.

11. The device according to claim 10 wherein said means for monitoring includes a voltmeter and current meter in electrical communication with said capacitor system.

12. The device according to claim 10 wherein said means for monitoring and correlating utilizes a low voltage charge applied to said capacitor system.

13. A method to automatically reform a capacitor system in an implantable cardioverter defibrillator comprising the device-implemented steps of:

(a) measuring an electrical parameter of the capacitor system; and (b) initiating a reform cycle if the measured electrical parameter is outside a preset value correlated to the electrical parameter.

14. The method according to claim 13 wherein step (a) further comprises the step of using said measured electrical parameter to determine a value correlated to an estimated charging time of the capacitor system and wherein step (b) is performed if the value indicates that an actual charging time would be greater than a predetermined maximum charging time.

15. The method of claim 14 wherein the electrical parameter measured in step (a) is a leakage current measured at a low voltage charge applied to the capacitor system and the value which is determined is a root mean square value of the leakage current which is compared to a preset value for leakage current in order to determine whether to initiate step (b).

16. An implantable defibrillator that produces a high voltage capacitive-discharge delivered to a human patient via a plurality of implantable electrodes comprising:

a low voltage battery system;

a transformer having a primary side and a secondary side, the primary side being connected to the battery system and to a flyback charging switch;

a high voltage capacitor system connected to the secondary side of the transformer by at least one diode;

an output switching network connected between the capacitor system and the plurality of implantable electrodes;

a sensing system that detects cardiac activity;

a control circuit electrically connected to the sensing system, the output switching network and the flyback charging switch to charge the capacitor system from the battery system in response to a cardiac dysrhythmia detected by the sensing system and then discharge the capacitor system through the switching network to the plurality of implantable electrodes;

a measurement circuit electrically connected to the capacitor system to measure at least one electrical parameter of the capacitor system; and a control unit connected to the measurement circuit and to the control circuit that initiates a capacitor reform cycle of charging the capacitor system from the battery system in the event that an estimated charging time of the capacitor system as calculated by the control unit based on the at least one electrical parameter is above a predetermined value.

17. The implantable defibrillator of claim 16 wherein the control unit periodically determines the estimated charging time based on an electrical parameter measured while the capacitor system is charged to a low voltage.

18. The implantable defibrillator of claim 16 wherein the electrical parameter is a leakage current of the capacitor system.

19. The implantable defibrillator of claim 16 wherein the electrical parameter is a charge time of the capacitor system to a low voltage.

* * * * *